United States Patent [19]
Logan et al.

[11] Patent Number: 5,686,254
[45] Date of Patent: Nov. 11, 1997

[54] REDUCTION IN FIRST SLIDE BIAS AND IMPROVED ENZYME STABILITY BY THE INCORPORATION OF DIARYL TELLURIDES IN THIN-FILM IMMUNOASSAY ELEMENTS

[75] Inventors: Margaret Elizabeth Logan; Carol Anne DeCann; Marsha Denise Bale Oenick, all of Rochester; Gary Louis Snodgrass, North Chili; Roy Eugene Snoke, Webster, all of N.Y.

[73] Assignee: Johnson & Johnson Clinical Diagnostics, Inc., Rochester, N.Y.

[21] Appl. No.: 476,155

[22] Filed: Jun. 7, 1995

[51] Int. Cl.$^6$ .................................................. G01N 33/53
[52] U.S. Cl. .................. 435/7.9; 435/4; 435/7.92; 435/7.93; 435/7.94; 435/7.95; 435/28; 435/962; 435/963; 435/969; 435/970; 436/518; 436/533; 436/534; 528/403; 562/899
[58] Field of Search ................. 435/4, 7.9, 7.92–7.95, 435/28, 962, 963, 969, 970; 436/518, 528–534; 528/395, 403, 405; 562/899

[56] References Cited

U.S. PATENT DOCUMENTS

| | | | |
|---|---|---|---|
| 4,113,496 | 9/1978 | Shiga et al. | 96/114.1 |
| 4,235,990 | 11/1980 | DiGiacomo et al. | 528/287 |
| 4,235,991 | 11/1980 | Digiacomo et al. | 528/391 |
| 4,256,872 | 3/1981 | Digiacomo et al. | 528/395 |
| 4,276,409 | 6/1981 | DiaGiacomo et al. | 528/362 |
| 4,276,410 | 6/1981 | DiGiacomo et al. | 528/373 |
| 4,276,411 | 6/1981 | Digiacomo et al. | 528/395 |
| 4,374,242 | 2/1983 | Dines et al. | 528/395 |
| 4,436,899 | 3/1984 | Digiacomo et al. | 528/395 |
| 4,487,922 | 12/1984 | Dines et al. | 528/395 |
| 4,607,000 | 8/1986 | Gunther et al. | 430/428 |
| 4,722,986 | 2/1988 | Young | 527/203 |
| 5,116,401 | 5/1992 | Young | 71/86 |
| 5,164,524 | 11/1992 | Gedridge, Jr. et al. | 556/423 |
| 5,250,397 | 10/1993 | Damada et al. | 430/359 |
| 5,273,859 | 12/1993 | Kaktoh et al. | 430/264 |
| 5,395,556 | 3/1995 | Drost et al. | 252/582 |

FOREIGN PATENT DOCUMENTS

WO93/16993   9/1993   WIPO.

*Primary Examiner*—Carol A. Spiegel

[57] ABSTRACT

A dry immunoassay analytical element for assaying a ligand, comprising a support bearing:

1. an enzyme labeled ligand or an enzyme labeled receptor zone;
2. a spreading zone; and
3. a receptor zone containing a fixed concentration of an immobilized receptor for the ligand and the labeled ligand when present and the receptor is covalently bonded to polymeric beads having a diameter in the range of 0.1 to 5 μm; characterized in that the element contains a diaryl telluride (DAT) compound and the zones can be in the same or separate layers.

11 Claims, 3 Drawing Sheets

REDUCTION IN FIRST SLIDE BIAS AND IMPROVED ENZYME STABILITY BY THE INCORPORATION OF DIARYL TELLURIDES IN THIN-FILM IMMUNOASSAY ELEMENTS

RELATED CASES

The present case is related to U.S. Pat. No 5,516,645 issued 5 May 1996 to Daniel S. Daniel, et al and entitled IMMUNOASSAY ANALYTICAL ELEMENTS CONTAINING VANADIUM IV ($V^{+4}$) IONS.

FIELD OF THE INVENTION

This invention relates to an immunoassay element and use thereof in an immunoassay.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes include, for example, antigens, antibodies, therapeutic drugs, narcotics, enzymes, hormones, proteins, etc.

The analyte, which is the target of the assay, is referred to herein as the ligand. Compounds which specifically recognize the ligand and react to form complexes with the ligand are referred to herein as receptors. The receptor and the ligand form a conjugate pair. Any member of the pair can function as a receptor or a ligand.

In the case of a competitive assay, a labeled analyte, including labeled immunocomponent derivatives and analogs of such analyte, are necessary components of the assay; whereas, in the case of a sandwich assay, a labeled receptor for the analyte is necessarily employed. These are referred to herein as the labeled ligand and labeled receptor, respectively.

In competitive binding immunoassays, a labeled ligand is placed in competition with unlabeled ligand for reaction with a fixed amount of the appropriate receptor. Unknown concentrations of the ligand can be determined from the measured signal of either the bound or unbound (i.e. free) labeled ligand. The reaction proceeds as follows:

In an alternative immunoassay format known as a "sandwich" immunoassay or immunometric assay, the ligand is contacted with two or more receptor molecules which bind to the ligand at different epitopic sites. One receptor is typically appropriately labeled and the other is either immobilized on a solid substrate or is capable of being immobilized thereon. The amount of ligand is directly proportional to the amount of bound complex among the ligand and the two receptors. This is illustrated as follows:

Conventional labels include radioactive tags, enzymes, chromophores, fluorophores, stable free radicals and enzyme cofactors, inhibitors and allosteric effectors.

Immunoassay analytical elements are known from U.S. Pat. Nos. 4,517,288 and 4,258,001. In general, such elements comprise receptors, such as antibodies for a ligand, immobilized in a particulate layer. In addition the element usually contains a reagent system that, through interaction with a bound or unbound species, results in a signal that can be correlated to the concentration of ligand in a sample. In use, the sample is manually combined with an enzyme labeled ligand and applied to the element. After a time, a solution containing a substrate for the labeled ligand is applied to the particulate layer. The reaction with the substrate is catalyzed by the enzyme label to form a reaction product that ultimately causes a signal color to develop. The reflection density of the color can be correlated to the concentration of the ligand in the sample. Similar signal development systems are known for other known conventional labels such as radioactive tags, chromophores, fluorophores, stable free radicals, and enzyme cofactors, inhibitors and allosteric effectors.

Multilayer immunoassay elements are thin film elements which use the above described immunoassay principles to measure analytes in fluid samples. In competitive assay elements, the rate of color formation is inversely correlated to the amount of analyte present and in sandwich assay elements, the rate of color formation is directly correlated to the amount of analyte present. Also, the rate of color formation is directly proportional to the activity of the enzyme labeled analyte, e.g. drug, or enzyme labeled receptor bound to the immobilized receptor. For the immunoassays to maintain a stable calibration, none of the enzyme activity (measured rate) can be lost in any of the slides during the specified calibration period.

Frequently, immunoassay elements are supplied to customers in plastic "cartridges" containing 50 separate elements from which one element may be removed at a time as needed. The elements are stacked one on top of another so that the lower 49 elements in the cartridge all have their top surfaces covered by the element above. However, the top element in the stack has no such covering and therefore the surface of that element is exposed to environmental factors to which the other 49 elements are not. For example, the top (or first) element is more exposed to air flow and light than the remainder of the elements when the cartridges are being handled during manufacturing or when the cartridges are in the element supplies of the clinical analyzers.

During storage, prior to use, the cartridges themselves are stored in sealed, foil-lined bags. However, the top element is still more exposed to the residual air and humidity inside the sealed bags than the other 49 elements.

It has been found that, when a common test fluid was reacted with the elements in a cartridge, the rate of color formation observed in the top (or first) element was always lower than the rate of color formation observed when the same test fluid was applied to elements below the top element in the same cartridge. This is referred to as first slide bias.

SUMMARY OF THE INVENTION

According to one aspect of the present invention, there is provided a dry immunoassay analytical element for assaying a ligand, comprising a support bearing:
 (a) an enzyme labeled ligand or an enzyme labeled receptor zone;
 (b) a spreading zone; and
 (c) a receptor zone containing a fixed concentration of an immobilized receptor for the ligand and the labeled ligand when present. In this case the receptor is covalently bonded to polymeric beads having a diameter in the range of 0.1 to 5 µm; characterized in that the element contains a diaryl telluride (DAT) compound and the zones can be in the same or separate layers.

The element defined above substantially reduces first slide bias, i.e. the altered rate of color development of the top element in a cartridge compared to the other elements in the same cartridge. Moreover all elements in the cartridge exhibit greater long term keeping. The examples establish that any diaryl telluride (DAT) compound provides these benefits.

In addition, the DAT compounds are useful in stabilizing enzyme compositions generally, particularly horseradish peroxidase (HRP) and conjugates in which such enzymes are used as labels. For example, the compounds can be used in solution assays as well as in the dry elements of this invention.

The present invention also provides a method for the assay of an immunologically reactive ligand in an aqueous liquid sample, comprising the steps of:

A. providing a dry immunoassay analytical element according to the present invention;

B. contacting a finite area of the top zone or layer of the element with sample of the liquid sample thereby forming: (i) an immobilized ligand receptor complex, (ii) an immobilized enzyme labeled ligand-receptor complex; or (iii) a mixture of (i) and (ii); or an immobilized receptor-ligand-labeled receptor complex;

C. contacting the finite area with a substrate solution thereby catalyzing the development of a color; and

D. determining the concentration of the ligand colorimetrically.

In the above method, the labeled receptor or labeled ligand is separated from the immobilized labeled ligand or immobilized labeled receptor. Such separation may be effected by any means known in the art, for example by the addition of a substrate solution, e.g. a hydrogen peroxide solution.

DETAILS OF THE INVENTION

The elements of this invention comprise labeled ligand or labeled receptor, spreading and receptor zones. The various zones can be in one coated layer or in separate coated layers. For example, the spreading zone and the receptor zone can be in a single layer or they can be in separate layers. The separate layers can be arranged in any order on the support. Or the separate layers can be arranged such that the receptor layer is directly on the support, the spreading layer directly above the receptor layer and the labeled ligand or labeled receptor zone over the spreading layer. When the receptor zone forms an entirely separate layer, the layer will also include a binder of the type describe hereinafter. The element can include additional layers such as those described infra. All such layers can be coated using coating techniques known in this art and which are briefly described infra.

The spreading layer or zone is porous. It contains, as an essential ingredient, a diaryl telluride. Representative compounds which are diaryl tellurides of the formula result in significant reductions in first slide bias when incorporated into the Human chorionic gonadotropin (hCG); or C-reactive protein (CRP) assay slides as described below. A subset of these compounds also preserve HRP activity in a model system designed to evaluate compounds or their ability to prevent first slide bias.

Useful diorganotellurides include materials where $Ar^1$ and $Ar^2$ represent the same or different aryl or heteroaryl groups, substituted or unsubstituted, with substituents which are defined below.

wherein X is O, S, Se, or Te, and $R^{11}$, $R^{12}$, $R^{13}$, $R^{21}$, $R^{22}$, $R^{23}$, $R^{31}$, $R^{32}$, $R^{33}$, $R^{41}$, $R^{42}$ and $R^{43}$ are the same or different and each selected from the group consisting of hydrogen, alkyl having 1–5 carbon atoms, OH, $OR^1$, SH, $NH_2$, $NHR^1$, $NR^1{}_2$, $NR^1R^2$, $CO_2H$ or its salts, $CO_2R^1$, $SO_3H$ and its salts, $PO_3H_2$ and its salts, and $SR^1$ wherein $R^1$ and $R^2$ are different and each selected from the group consisting of alkyl having a carbon chain of 1 to 14 carbon atoms optionally carrying one or several hydrophilic groups, phenyl, and substituted phenyl.

$R^{14}$, $R^{15}$, $R^{24}$, and $R^{25}$ are the same or different and each selected from the group consisting of hydrogen, alkyl having 1–5 carbon atoms, alkoxy having 1–5 carbon atoms, $CO_2H$ or its salts, $CO_2R^1$, $SO_3H$ and its salts, $PO_3H_2$ and its salts where $R^1$ is as described above.

In the above, alkyl shall mean groups such as methyl, ethyl, propyl, isopropyl, n-butyl, sec-butyl, tert-butyl, amyl, isoamyl, or neopentyl.

A carbon chain with 1–5 carbon atoms shall mean a straight or branched carbon chain, such as methyl, ethyl, propyl, isopropyl, n-butyl, sec-butyl, tert-butyl, amyl, isoamyl, or neopentyl.

A carbon chain with 1–14 carbon atoms shall include, but not be limited to, methyl, ethyl, propyl, isopropyl, n-butyl, sec-butyl, tert-butyl, amyl, isoamyl, neopentyl, hexyl, octyl, decyl, tetradecyl and the like.

Hydrophilic groups mean groups such as sulfonic, phosphonic or carboxylic acid, hydroxyl, and amino groups. Some of these compounds can form salts with either acids or bases. Sodium, potassium, ammonium, calcium and magnesium salts and salts with hydrochloric, hydrobromic, phosphoric, and sulfuric acids and with organic acids such as oxalic, fumaric, tartaric, malonic, acetic, citric, and succinic acids, are preferred.

Preferred DAT's are those having substituents on the aromatic ring that contain groups that confer water solubility, such as, but not limited to, hydroxyl groups, amines and their salts, and carboxylic acids and their salts. In particular, water soluble compounds that preserve HRP activity either alone or in cooperation with vanadyl compounds are as follows.

Other materials for use in spreading layers are well known in the art of making dry analytical elements as disclosed, for example, in U.S. Pat. No. 4,258,001. Such layers include macroporous layers made from cloth, paper, etc. A preferred particulate layer is a bead spreading layer (BSL). This layer can be easily constructed to have suitable porosity for use in the elements of the present invention to accommodate a test sample (e.g. 1 to 100 μL), diluted or undiluted. Preferably, the spreading layer is isotropically porous, which property is created by interconnected spaces between the particles comprising the zone. By isotropically porous is meant that the spreading layer uniformly spreads the applied fluid in all directions throughout the layer.

Useful spreading layers, including bead spreading layers are disclosed in U.S. Pat. Nos. 4,670,381; 4,258,001 and 4,430,436. Particularly useful spreading layers are those having a particulate structure formed by organo-polymeric particles and a polymeric adhesive for those particles described in U.S. Pat. No. 4,258,001. The organo-polymeric particles useful in the spreading layer are generally heatstable, spherical beads having a particle size in the range of from about 10 to 40 μm in diameter or even smaller.

The particles can be composed of a wide variety of organic polymers, including both natural and synthetic polymers, having the requisite properties. Preferably, however, they are composed of one or more addition polymers described in the aforementioned patents.

When the receptor layer is a separate layer, it is prepared and coated over a support or over a reagent layer or subbing layer on the support. The receptors are covalently bonded to polymer particles through surface reactive groups on the receptor (nucleophilic free amino groups and sulfhydryl groups).

A general procedure for attaching receptors to the small polymer beads includes covalently attaching the selected receptor to the beads using generally known reactions. With many pendant groups, for example the haloalkyl, 2-substituted activated ethylsulfonyl and vinylsulfonyl, the receptor can be directly attached to the beads. Generally, the beads are mixed with the receptor in an aqueous buffered solution (pH generally from about 5 to about 10) and a concentration of from about 0.1 to about 40 weight percent polymer particles (preferably from about 0.1 to about 10 weight percent). The amount of receptor is at a ratio to polymer of from about 0.1:1000 to about 1:10, and preferably from about 1:100 to about 1:10. Mixing is carried out at a temperature in the range of from about 5 to about 50° C., and preferably at from about 5 to about 40° C., for from about 0.5 to about 48 hours. Any suitable buffer can be used.

In some instances, the pendant reactive groups on the outer surface must be modified or activated in order to cause covalent attachment of the ligand. For example, carboxyl groups must be activated using known carbodiimide or carbamoylonium chemistry, described in EP 308235 published 22 Jul. 1992 and U.S. Pat. No. 5,155,166.

The attachment of the receptor to carboxyl group-containing monodispersed polymer beads, however, is carried out in two steps, the first of which involves contacting an aqueous suspension of the particles with a carbodiimide or a carbamoylonium compound to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 7. The molar ratio of carbodiimide or carbamoylonium compound to the carboxyl groups on the surface of the particles is from about 10:1 to 500:1.

In the second step of the method, the reactive intermediate formed in the first step is contacted with a reactive amine- or sulfhydryl-group containing receptor. A covalent linkage is thereby formed between the particles and the receptor. The weight ratio of the receptor to the polymeric particles is generally from about 1:1000 to about 1:1, and preferably from about 1:100 to about 1:10.

In other instances, an epoxy group on the outer surface can be hydrolyzed to form a diol compound capable of reacting with cyanogen bromide which can act as a coupling agent for amine groups in the immunological species. Aldehydes can react directly with amines to form a Schiff's base which can be subsequently reduced to form a covalent link. Alternatively, the aldehyde can be oxidized to an acid and chemistry identified above for carboxyl groups can be used to form an amide linkage.

Any reactive amine- or sulfhydryl-containing receptor can be attached to the monodispersed polymeric beads as long as that receptor contains a reactive amine or sulfhydryl group, respectively, which will read with the reactive groups on the polymer or with the intermediate formed by the reaction of a carbodiimide or a carbamoylonium compound with carboxyl groups on the particles in the case which the polymer has reactive carboxyl groups.

The small polymer beads having reactive groups that readily read directly with the amine or sulfhydryl groups on the receptors are simply mixed with the receptors, in an appropriate buffer if necessary, and allowed to react.

Polymers from which beads for the receptor can be selected include the following: poly(m & p-chloromethylstyrene), poly(styrene-co-m & p chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl) phenyl]acrylamide}(99.3:0.7 molar ratio), poly(m & p-chloromethylstyrene-co-methacrylic acid) (95:5, 98:2 and 99.8:0.2 molar ratio), poly(styrene-co-m & p-chloroethylsulfonylmethyl styrene-co-methacrylic acid) (93.5:4. 5:2 molar ratio) poly{styrene-co-N-[m & p-(2-chloroethylsulfonylmethyl)phenyl]acrylamide-co-methacrylic acid}(97.3:0.7:2 molar ratio), poly(styrene-co-m & p-chloromethylstyrene)(70:30 molar ratio), poly [styrene-co-3-(p-vinylbenzylthio)propionic acid] (97.6:2.4 molar ratio), poly(styrene-co-vinylbenzyl chloride-coacrylic acid)(85:10:5 molar ratio), poly(styrene-co-acrylic acid) (99:1 molar ratio), poly(styrene-co-methacrylic acid) (90:10 molar ratio), poly(styrene-co-acrylic acid-co-m & p-divinylbenzene) (89:10:1 molar ratio), poly(styrene-co-2-carboxyethyl acrylate)(90:10 molar ratio), poly(methyl methacrylate-co-acrylic acid) (70:30 molar ratio), poly (styrene-co-m & p-vinylbenzaldehyde)(95:5 molar ratio), and poly(styrene-co-m & p-vinylbenzaldehyde-co-methacrylic acid)(93:5:2 molar ratio).

The layers of the element are carried on a suitable support. The receptor layer is coated over the support although there may be intervening layers, such as a gelatin/buffer layer, between the support and the receptor layer. The support can be any suitable dimensionally stable and, preferably, non-porous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

Polymeric binders for the receptor layer are described generally in Canadian patent 1,240,445 and are expressly incorporated herein by reference. Useful polymers are polymers comprising from about 30 to 97 weight percent of polymerized N-alkyl substituted acrylamide such as N-isopropylacrylamide. Other useful N-alkyl-substituted acrylamides include N-n-butylacrylamide, N,N-diethylacrylamide and N-n-propylacrylamide. Poly(N-isopropylacrylamide-co-methacrylic acid-co-N,N'-methylenebisacrylamide is used in the examples to illustrate the utility of these binders.

The polymer binder also comprises from about 3 to 25 weight percent of one or more polymerized crosslinking monomers having at least two addition-polymerizable groups per molecule. These crosslinking monomers are generally well known in the art. The preferred crosslinking monomers contain acrylamido or methacrylamido groups to facilitate polymerization with the N-alkyl-substituted acrylamides.

Examples of useful crosslinking monomers include:
N,N'-methylenebisacrylamide;
N,N'-methylenebismethacrylamide;
ethylene dimethacrylate;
2,2-dimethyl-1,3-propylene diacrylate;
divinylbenzene;
mono[2,3-bis(methacryloyloxy)propyl] phosphate;
N,N'-bis(methacryloyl)urea;
triallyl cyanurate;
allyl acrylate;
allyl methacrylate;
N-allylmethacrylamide;
4,4'-isopropylidenediphenylene diacrylate;
1,3-butylene diacrylate;
1,4-cyclohexylenedimethylene dimethacrylate;
2,2'-oxydiethylene dimethacrylate;
divinyloxymethane;
ethylene diacrylate;
ethylidene diacrylate;
propylidene dimethacrylate;
1,6-diacrylamidohexane;
1,6-hexamethylene diacrylate;
1,6-hexamethylene dimethacrylate;
phenylethylene dimethacrylate;
tetramethylene dimethacrylate;
2,2,2-trichloroethylidene dimethacrylate;
ethylenebis(oxyethylene) diacrylate;
ethylenebis(oxyethylene) dimethacrylate;
ethylidyne trimethacrylate;
propylidyne triacrylate;
vinyl allyloxyacetate;
1-vinyloxy-2-allyloxyethane;
2-crotonoyloxyethyl methacrylate;
diallyl phthalate; and
2-(5-phenyl-2,4-pentadienoyloxy)ethyl methacrylate.

These polymeric binders can also include 0 to 60 weight percent of polymerized hydrophilic monomers. Amounts of 5 to 35 weight percent are also useful. Hydrophilic monomers are disclosed in Canadian patent 1,240,445. In particular, such monomers have one or more groups selected from hydroxy, pyrrolidone, amine, amide, carboxy, sulfo, carboxylate salt, sulfonate salt and sulfate salt groups. Generally the counter ions of the salt groups are alkali metal or ammonium. Useful hydrophilic monomers are acrylic acid and methacrylic acid and their salts, sodium 2-acrylamido-2-methylpropane sulfonate, 2-hydroxyethyl acrylate, 2-hydroxyethyl methacrylate, 2-hydroxypropyl acrylate, 2-hydroxypropyl methacrylate and glyceryl methacrylate.

Further, the recited binders make it possible to form uniform coatings of receptor layers due to the very low binder viscosities achieved from sheer thinning during extrusion hopper coating. A further advantage is achieved with the recited binders in that, immediately after forming uniform coatings, the viscosity of the binders increases substantially, resulting in a "set layer" that remains stable and uniform during wet transport and drying of the binders.

The receptors also can be dispersed in a polymer binder selected from the group consisting of:
poly(vinyl alcohol);
bovine serum albumin;
acacia gum;
homopolymers of N-vinylpyrrolidone having a molecular weight in the range 8000 to 400,000; and water-soluble vinyl addition copolymers having two or more monomers selected from the group consisting of acrylamide, methacrylamide, N-alkyl-substituted acrylamides, N-alkyl substituted methacrylamides, 1-vinylimidazole, 2-alkyl substituted-1-vinylimidazoles, 2-hydroxyalkyl substituted-1-vinylimidazoles, N-vinylpyrrolidone, hydroxyalkyl acrylates, hydroxyalkyl methacrylates, acrylic acid, and methacrylic acid; wherein alkyl and hydroxyalkyl in the copolymers has 1 to 6 carbon atoms such methyl, ethyl, propyl and hexyl.

The element can comprise one or more additional layers, e.g. separate or combined reagent/spreading layer and a gelatin/buffer layer containing other necessary additives such as electron transfer agents.

The gelatin/buffer layer or the reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly (vinylpyrrolidone), poly(N-isopropylacrylamide), poly (acrylamide-co-N-vinyl-2-pyrrolidone) and similar copolymers. The indicator composition also can be dispersed in the receptor layer.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, coupler solvents, and other materials known in the art. The amounts of these components are also within the skill of a worker in the art.

The elements can be used to determine low concentrations of immunologically reactive ligands in a liquid, such as a biological fluid (e.g., whole blood, serum, plasma, urine, spinal fluid, suspensions of human or animal tissue, feces, saliva, lymphatic fluid and the like). The ligands can be determined at concentrations as low as about $10^{-15}$ molar, and most generally at a concentration of from about $10^{-11}$ to about $10^{-4}$ molar.

Ligands which can be so determined, either quantitatively or qualitatively, include therapeutic drugs (e.g., phenobarbital, digoxin, digitoxin, theophylline, gentamicin, quinidine, phenytoin, propanolol, carbamazepine, tobramycin, lidocaine, procainamide and the like), natural or synthetic steroids (e.g. cortisol, aldosterone, testosterone, progesterone, estriol, etc.), hormones (e.g. thyroid hormones, peptide hormones, insulin, etc.), proteins (e.g. albumin, IgG, IgM, ferritin, blood clotting factors, C-reactive protein, isoenzymes, hCG, apolipoproteins, etc.), antigens, antibodies including monoclonal antibodies, and other species which will naturally react with a receptor. This invention is particularly useful for the determination of therapeutic drugs, such as digoxin, phenytoin, carbamazepine, theophylline, or phenobarbital, hormones such as thyroxine or triiodothyronine and analytes such as hCG and C-reative protein.

The assay can be carried out using any enzyme label which can be attached to the ligand to form a labeled ligand. Enzymes, such as glucose oxidase, peroxidases such as horseradish peroxidase (HRP), alkaline phosphatase and galactosidase are preferred labels.

It is within the skill of the ordinary worker in clinical chemistry to determine a suitable substrate for a given label. The substrate can be a material which is directly acted upon by the enzyme label or a material that is involved in a series of reactions which involve enzymatic reaction of the label. For example, if the enzyme label is a peroxidase, the substrate is hydrogen peroxide plus an appropriate reducing agent. Using glucose oxidase as an example, the substrate glucose is generally present in the reagent layer or added as a substrate solution to yield about 0.01 mole/m$^2$, and preferably from about 0.001 to about 0.1 mole/m$^2$. A worker skilled in the art would know how to adjust the amount of a particular substrate for the amount of enzyme label used in the assay.

The reagent layer may contain an indicator composition comprising one or more reagents which provide a detectable species as a result of the reaction catalyzed by the label. The detectable species could develop a color, be radioactive, fluoresce, or be chemiluminescent. For present purposes the invention is illustrated using a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction or a combination of reagents which produce the dye. For example, when glucose is used as the substrate and glucose oxidase as the enzyme label, the colorimetric indicator composition can include a coupler and an oxidizable compound which react to provide a dye. Alternatively, the composition can include a leuco dye and peroxidase or another suitable peroxidative compound which generates a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Pat. No. 4,670,385 (issued 2 Jun. 1987 to Babb et al.) The particular amounts of the colorimetric indicator composition and its various components are within the skill of a worker in the art.

The labeled ligands can be prepared using known starting materials and procedures, or obtained commercially. Generally, the ligand is attached to the label (e.g. an enzyme moiety) through a covalent bond.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 µL. The finite area which is contacted is generally no more than about 150 mm$^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable spectrophotometric apparatus using generally known procedures. In an enzymatic reaction, the resulting product is determined by measuring, for example, the rate of change of reflection or transmission density in the finite area which was contacted with the test sample. The area which is measured has a diameter of generally from about 3 to about 5 min. The amount of ligand in the liquid sample is inversely proportional to the amount of label measured in the finite area in the case of a competitive assay, or is directly proportional in the case of a sandwich assay. Generally, label measurement is made after application of a substrate solution.

DETAILED DESCRIPTION OF THE INVENTION

1. Synthesis of the diaryl tellurides.

There exist many synthetic routes to prepare DATs. The route used for a particular compound depends heavily on the substituents on the aromatic rings. Several of the known routes are illustrated in the examples below. Extrapolation of these and other literature methods to the synthesis of other DAT's should be readily apparent.

Preparation 1. 4,4'-Di(2-hydroxyethoxy)-1,1'-tellurobisbenzene (1)

(a) Preparation of [2-(4-Bromophenoxy)ethoxy](1,1-dimethylethyl)dimethylsilane (1a)

To a solution of [2-(4-bromophenoxy)ethanol (10.0 g, 46 mmol) in 150 mL dry dimethylformamide (30 mL) was added t-butyldimethylsilyl chloride (8.34 g, 55 mmol) and imidazole (7.82 g, 115 mmol). Additional dimethylformamide (20 mL) was used to wash these materials into the reaction flask. The resulting solution was stirred overnight at rt with a Newman tube. It was poured onto water (200 mL) and extracted with ether (3×75 mL). The combined extracts were washed with 0.5N HCl (200 mL), sat. NaHCO$_3$ (200 mL), water (4∴ 150 mL), and sat. NaCl (200 mL), dried over MgSO$_4$, and filtered. The solvent was removed under reduced pressure on a rotary evaporator to give the crude product (16.5 g; >100%). $^1$H NMR (CDCl$_3$) δ7.34 (2H, d, J=8.9), 6.78 (2H, d, J=8.9), 4.00–3.93 (4H, m), 0.89 (9H, s), 0.08 (6H, s). $^{13}$C NMR (CDCl$_3$) δ158.1, 132.2, 116.4, 112.8, 69.6, 61.9, 25.9, 18.4. FDMS (m/e) 330 (M$^+$, $^{79}$Br). It was used as 100% without purification.

(b) Preparation of 4,4'-Di(2-hydroxyethoxy)-1,1'-tellurobisbenzene (1)

A 500 mL 3-neck flask, was placed under argon and equipped with a condenser and an addition funnel. Magnesium turnings (0.89 g, 37 mmol) were added. Bromide 1a (12.3 g, 37 mmol, used as 100%) was taken up in dry tetrahydrofuran (THF) (100 mL), and transferred to the addition funnel. The Grignard reaction was initiated with approximately 10 mL of the bromide solution, 1,2-dibromoethane, and iodine. The remaining bromide solution was added and the reaction was refluxed overnight, after which time no Mg remained. The heating mantle was removed for 30 min, then tellurium granules (4.74 g, 37 mmol) were added, and the reaction was heated back to reflux for 7 h, at which time nearly all the Te had been consumed. The reaction was cooled to rt, then poured onto rapidly stirring 10% aq. NH$_4$Cl (300 mL) and stirred for 15 min. Precipitated Te was removed by filtration through Celite diatomaceous earth and the filter cake was washed with ether. The filtrate was transferred to a separatory funnel and extracted three times with ether (200 mL, 100 mL, 100 mL). The combined extracts were washed with water and sat. NaCl, dried over MgSO$_4$, and filtered. The solvent was removed under reduced pressure to give the crude product (12.4 g) as a red oil. It was taken up in toluene (50 mL) with copper powder (2.5 g), and heated to reflux with a Newman tube for 2.5 h, at which time the color had turned from red to gray. The reaction was cooled to rt, filtered through Celite diatomaceous earth, washed with ether, and concentrated, giving an amber oil (12.4 g). By $^1$H NMR, it was a mixture of the desired product, quenched Grignard, and residual toluene. It was taken up in methanol (50 mL) and (50 mL) and THF (20 mL) with potassium fluoride (5.0 25, 86 mmol), and refluxed for 24 h. The bulk of the methanol was removed under reduced pressure, and partitioned between ether-ethyl acetate and water. The aqueous phase was extracted twice more with ethyl acetate, and the combined extracts were washed with water and sat. NaCl, dried over Na$_2$SO$_4$, and filtered. The solvent was removed under reduced pressure to give the crude product (8 g) as a tan solid. Ether trituration gave a white solid that was isolated by filtration, washed with ether, and air dried, to give the crude product (1.74 g). It was adsorbed onto flash silica gel (20 mL) using dichloromethane. Careful flash chromatography on 200 mL flash silica gel, eluting with dichloromethane then 95:5 dichloromethane:methanol (the product elutes just before a small amount of the corresponding biaryl compound), ether trituration and filtration gave pure 1 as a white solid (1.2 g). The ether filtrate from the trituration of the crude product was chromatographed as above. Ether trituration and recrystallization from ethanol gave additional pure 1 (0.2 g). Total yield: 1.4 g, 19%. $^1$H NMR (DMSO-d$_6$) δ7.52 (4H, d, J=8.5), 6.80 (4H, d, J=8.5), 4.82 (2H, t, J=5.5), 3.91 (4H, t, J=5.0), 3.65 (4H, app q, J=5.1). $^{13}$C NMR (DMSO-δ$_6$) δ159.2, 139.8, 116.5, 104.5, 69.9, 59.9. FDMS (m/e) 404 (M$^+$, $^{130}$Te).

Preparation 2. N,N-Dimethyl-2-(phenyltelluro)benzenemethanamine, Hydrochloride Salt (2)

(a) Preparation of N,N-Dimethyl-2-(phenyltelluro)benzenemethanamine (2a)

To a solution of N,N-dimethylbenzenemethanamine (2.70 g, 0.020 mol) in dry ether (50 mL) in a round-bottom flask under argon at rt was added n-BuLi (2.5M, 10 mL, 0.025 mol) dropwise by syringe. The reaction was stirred 5 h at rt, then a solution of phenyltellurenyl bromide in dry tetrahydrofuran (0.5M) was added dropwise by syringe. After the addition of 38 mL (0.019 mol), the reaction turned the characteristic orange of the phenyltellurenyl bromide, and the addition was stopped. The reaction mixture was poured onto ether (100 mL), and the resulting solution was washed with sat. NaCl (1×100 mL, 2×50 mL), dried over MgSO$_4$, and concentrated. The residue was dissolved in acetone (100 mL), and iodine (5.08 g, 0.020 mol) was added. The resulting solution was chilled to precipitate the product. The yellow crystals were collected by filtration, washed with cold acetone, and dried to give the iodine adduct of 2a (5.95 g, 50%, mp 178°–179°). The iodine adduct (5.93 g, 0.010 mol) was dissolved in dimethylformamide (100 mL). Sodium bisulfite (5.2 g, 0.05 mol) in water (100 mL) was slowly added, and the reaction was stirred 1 h at rt, during which time the reaction became colorless. The reaction was poured onto water (500 mL), then washed with ether (2×50). The aqueous layer was made basic with 10% NaOH, and the amine was extracted into ether (3×100 mL). The combined extracts were washed with sat. NaCl, dried over MgSO$_4$, and concentrated. The residue was recrystallized from methanol to give the pure product (3.14 g, 93%) as a white solid (mp51°–54°). $^1$H NMR (CDCl$_3$) δ7.88 (2H, d, J=6.9), 7.35 (1H, t, J=7.3), 7.26 (2H, t, J=7.3), 7.17 (1H, d, J=7.7), 7.10–7.04 (2H, m), 6.94–6.89 (1H, m), 3.53 (2H, s), 2.25 (6H, s).

(b) Preparation of N,N-Dimethyl-2-(phenyltelluro)benzenemethanamine, Hydrochloride Salt (2)

To a slurry of 2-(N,N-dimethylaminomethyl)-1-phenyltellurobenzene (1.02 g, 3.0 mmol) in ether (50 mL) in a water bath was added dropwise by syringe a hydrogen chloride/ether solution (3.15 mL, 1.0M, 3.15 mmol). The thick slurry was diluted with isopropanol (20 mL) then filtered. The white solid was washed with ether, and air dried, to give the product (1.13 g, 95%). $^1$H NMR (CDCl$_3$) δ2.6 (1H, br s), 8.13 (1H, d, J=7.5), 7.80 (1H, d, J=7.7), 7.52–7.48 (3H, m), 7.26–7.17 (4H, m), 4.44 (2H, d, J=5.8), 2.68 (6H, d, J=4.5). Anal. calc'd for C$_{15}$H$_{18}$ClNTe: C, 48.00; H, 4.83; N, 3.73. Found: C, 47.97; H, 4.87; N, 3.65.

Preparation 3. N,N,N',N'-Tetra(2-hydroxyethyl)-4,4'-tellurobisbenzenamine (3)

(a) Preparation of N,N-Bis[2-[[(1,1-dimethylethyl)dimethylsilyl]oxy]ethyl]benzenamine (3a)

A procedure analogous to that used for 1a was used with the following materials: 2,2'-(phenylimino)diethanol (9.0 g, 50 mmol), t-butyldimethylsilyl chloride (18.1 g, 0.12 mol), imidazole (17.0 g, 0.25 mol), and dimethylformamide (50 mL). The reaction was stirred overnight for convenience. Workup as in 1a gave 3a as a pale oil (21.6 g, >100%). $^1$H NMR (CDCl$_3$) δ7.21 (2H, d, J=8.4), 6.68 (3H, overlapping d, t), 3.77 (4H, d, J=6.6), 3.52 (4H, d, J=6.6), 0.92 (18H, s), 0.06 (12H, s). $^{13}$C NMR (CDCl$_3$) δ147.8, 129.2, 115.7, 111.4, 60.3, 53.5, 25.9, 18.3, −5.3. FDMS (m/e) 409 (M$^+$). It was used as 100% without purification.

(b) Preparation of N,N,N',N'-Tetra[2-[[(1,1-dimethylethyl)dimethylsilyl]oxy]ethyl]-4,4'-tellurobisbenzenamine (3b)

To a 500 mL 3-neck flask, oven-dried and put under argon was added tellurium (IV) chloride (5.93 g, 22 mmol). Dry ether (100 mL) was added by syringe, giving a thin yellow slurry, and the flask was placed in a water bath. A solution of 3a (18 g, 44 mmol) in dry ether (50 mL) was prepared under argon, and the solution was transferred by cannula to the reaction, with vigorous stirring. Initially a very thick yellow precipitate formed, which thinned out as the addition of the aniline solution continued. At the completion of the addition, the greenish yellow slurry was stirred overnight. The reaction was filtered, and the filtrate evaporated under reduced pressure. The resulting yellow-green oil was taken up in dichloromethane (200 mL), and a solution of sodium metabisulfite (8.36 g, 44 mmol) in water (200 mL) was added with stirring. The resulting two-phase mixture was stirred 30 min at rt, then filtered through Celite diatomaceous earth. Solid NaHCO$_3$ was added to pH 9, then the reaction was transferred to a separatory funnel. The dichloromethane layer was split off, and the aqueous layer was extracted with additional dichloromethane. The combined extracts were washed with water/sat. NaCl (200 mL/50 mL) then sat. NaCl, dried over Na$_2$SO$_4$, and filtered, and the solvent was removed under reduced pressure. The resulting red oil (21.4 g) was taken up in toluene (80 mL), and copper powder (4 g) was added. The reaction was heated to reflux with a Newman tube overnight. The resulting gray reaction was cooled to room temperature, filtered through Celite diatomaceous earth, and the solvent was removed under reduced pressure. The resulting amber oil (18 g) was flash chromatographed twice with 3:1 cyclohexane:dichloromethane to separate the product from recovered starting material, yielding pure 3b as a yellow oil (5.0 g, 48% of theory). $^1$H NMR (CDCl$_3$) δ7.54 (4H, d, J=8.6), 6.53 (4H, d, J=8.5), 3.72 (4H, t, J=6.4), 3.47 (4H, t, J=6.5), 0.88 (18H, s), 0.03 (12H, s). $^{13}$C NMR (CDCl$_3$) δ147.6, 139.7, 112.7, 98.2, 60.2, 53.4, 25.9, 18.3, −5.3. FDMS (m/e) 946 (M$^+$, $^{130}$Te).

(c) Preparation of N,N,N',N'-Tetra(2-hydroxyethyl)-4,4'-tellurobisbenzenamine (3)

A heterogeneous mixture of silyl ether 3b (2.7 g, 2.86 mmol), potassium fluoride (0.66 g, 11.4 mmol), and methanol (20 mL) was heated to reflux for 20 h. The white slurry was cooled in an ice bath, then the product was isolated by filtration, washed with cold methanol, and air dried (0.80 g, 57%). A small amount was recrystallized from methanol for an analytical sample (mp 169°–170°). $^1$H NMR (DMSO-d$_6$) δ7.54 (4H, d, J=8.6), 6.53 (4H, d, J=8.5), 3.45 (4H, app q, J=5.7), 3.33 (4H, t, J=5.9). $^{13}$C NMR (DMSO-d$_6$) δ148.1, 139.8, 113.1, 97.6, 58.4, 53.5. IR (KBr) 3350, 1585, 1495, 1350 cm$^{-1}$. FDMS (m/e) 490 (M$^+$, $^{130}$Te). Anal. calc'd for C$_{20}$H$_{28}$N$_2$O$_4$Te: C, 49.22; H, 5.78; N, 5.74. Found: C, 48.78; H, 5.72; N, 5.66.

Preparation 4. 2,2'-[Tellurobis(4,1-phenyleneoxy)]bisacetic Acid, Disodium Salt (4)

(a) Preparation of 4-(Bromophenoxy)(1,1-dimethlyethyl)dimethylsilane (4a)

To a solution of p-bromophenol (104 g, 0.6 mol) in dry dimethylformamide (450 mL) was added t-butyldimethylsilyl chloride (108 g, 0.72 mol) and imidazole (102 g, 1.5 mol). The resulting pale yellow solution was stirred 3 h at rt with a Newman tube. It was poured onto water (1.2 L) and extracted three times with ether (900 mL, 300 mL, 300 mL). The combined extracts were washed four times with water (150 mL), once with 1N HCl (300 mL), sat. NaHCO$_3$ (300 mL), and sat. NaCl (300 mL), dried over MgSO$_4$, and filtered. The solvent was removed under reduced pressure on a rotary evaporator then a vacuum pump to give the crude product (183 g; >100%), as a 6:1 ratio with the silanol from hydrolyzed starting material. $^1$H NMR (CDCl$_3$) δ7.31 (2H, d, J=8.7), 6.71 (2H, δ, J=8.7), 0.97 (9H, s), 0.18 (6H, s). It was used as 100% without purification.

(b) Preparation of 4,4'-Di(t-butyldimethylsilyloxy)-1,1'-tellurobisbenzene (4b)

A 2 L 3-neck flask, oven dried then placed under argon, was equipped with an overhead stirrer and an addition funnel. Magnesium turnings (15.2 g, 0.66 mol) were added. Bromide 4a (17.2 g, 0.6 mol, used as 100%) was taken up in dry THF (600 mL), and transferred to the addition funnel. The Grignard reaction was initiated with approximately 25 mL of the bromide solution and several crystals of iodine. The remaining bromide solution was added at such a rate that the reaction continued to reflux. The reaction was refluxed for an additional 30 min after the addition was complete, at which time only a small amount of Mg remained. The reaction was cooled slightly in a water bath, tellurium granules (76.8 g, 0.6 mol) were added, and the reaction was heated back to reflux for 2.5 h, at which time nearly all the Te had been consumed. The reaction was cooled to rt, then poured onto rapidly stirring 10% aq. NH$_4$Cl (2 L) and stirred for 30 min. Precipitated Te was removed by filtration through Celite diatomaceous earth, and the filter cake was washed with ether. The filtrate was transferred to a separatory funnel and extracted three times with ether (1200 mL, 300 mL, 300 mL). The combined extracts were washed with water and sat. NaCl, dried over MgSO$_4$, and filtered through Celite diatomaceous earth to remove both the MgSO$_4$ and Te which had precipitated during the workup. The solvent was removed under reduced pressure to give the crude product (194 g) as a red oil. It was taken up in toluene (900 mL) with copper powder (38 g), and heated to reflux with a Newman tube for 2.5 h, at which time the color had turned from red to gray. The reaction was cooled to rt, filtered through Celite diatomaceous earth, and concentrated, giving an amber oil (181 g). By $^1$H NMR, it was a mixture of the desired product, quenched Grignard, and residual toluene, and was calculated to contain 0.23 mol of 4b. Purification was effected via the iodine adduct of 4b. The crude product was taken up in acetone (0.6 L), and iodine (58 g, 0.23 mol) was added portionwise with vigorous stirring. After 15 min, a very thick precipitate had formed. Ethanol (1.2 L) was added, and the orange solid and dark iridescent crystalline solid were isolated by filtration and air-dried. A second crop was obtained by refiltration of the filtrate. The combined yield was 206 g, and it was pure by NMR, the only contaminant being residual ethanol. $^1$H NMR (CDCl$_3$) δ7.95 (4H, d, J=8.7), 6.86 (4H, d, J=8.7), 0.98 (18H, s), 0.25 (12H, s). $^{13}$C NMR (CDCl$_3$) δ158.6, 138.4, 121.9, 25.5, 18.2, −4.3. The iodine adduct was taken up in dioxane (500 mL), dichloromethane (500 mL), and 5% aq. NaHSO$_3$ (1.1 L) and the two-phase system was stirred vigorously. After 1 h, the lower (organic) layer was still red, indicative of incomplete reduction. The bulk of the yellow aqueous layer was decanted and saved, and the organic layer was evaporated under reduced pressure. Dioxane (200 mL), dichloromethane (200 mL), and 5% aq. NaHSO$_3$ (400 mL) were added to the residue, and the mixture was stirred an additional hour. It was evaporated under reduced pressure to partially remove the organic solvents, and the remaining aqueous dioxane was transferred to a separatory funnel and extracted three times with ether. The combined extracts were washed with water, sat. NaHCO$_3$, and sat. NaCl, dried over MgSO$_4$, and filtered. The decanted aqueous layer from above was worked up in the same way, and the two were combined. The solvent was removed under reduced pressure to give pure 4b (97.3 g, 60%) as an mber oil. $^1$H NMR (CDCl$_3$) δ7.54 (4H, d, J=8.4), 6.80 (4H, d, J=8.4), 0.96 (18H, s), 0.17 (12H, s). $^{13}$C NMR (CDCl$_3$) δ155.8, 139.6, 121.5, 105.2, 25.7, 18.2, −4.4. FDMS (m/e) 544 (M$^+$, $^{130}$Te).

(c) Preparation of 4,4'-Tellurobisphenol (4c)

Silyl ether 4b (54.2 g, 0.1 mol) was taken up in methanol (200 mL) in a 500 mL round bottom flask. Potassium fluoride (11.6 g, 0.2 mol) was added, and the reaction was heated to reflux for 1.5 h under argon. After the reaction was cooled to rt, it was poured into rapidly stirring water (1.2 L), using additional methanol (20 mL) to facilitate the transfer. The pH was adjusted to 14 with 10% NaOH (approx. 40 mL), and the reaction was filtered through Celite diatomaceous earth. The filtrate was transferred to a separatory funnel and washed twice with dichloromethane. The aqueous layer was transferred to a 2 L Edenmeyer flask in an ice bath, and 25% aq. acetic acid was added to pH 6, resulting in formation of a cream-colored precipitate. The product was isolated by filtration, washed with water, and air dried, to give the crude product (29 g). It was adsorbed onto flash silica gel (150 mL) using ether. Vacuum chromotography on 1 L flash silica gel, eluting with dichloromethane then 1:4 ethyl acetate:dichloromethane gave the pure product. Trituration with dichloromethane gave, in two crops, pure 4c as a yellow solid (24 g, 76%). $^1$H NMR (CDCl$_3$, 5 drops DMSO) δ8.77 (2H, s), 7.29 (4H, d, J=8.4), 6.47 (4H, d, J=8.4).

(d) Preparation of 4,4'-Di(ethoxycarbonylmethoxy)-1,1'-tellurobisbenzene (4d)

A 250 mL oven-dried 3-neck flask equipped with an overhead stirrer and an addition funnel was put under argon, and sodium hydride (60%, 1.76 g, 44 mmol) was added. It was washed with cyclohexane three times, then dry (sieves) dimethylformamide (60 mL) was added. The flask was placed in a water bath, and a solution of bisphenol 4c (6.28 g, 20 mmol) in dry dimethylformamide (15 mL) was added dropwise from the addition funnel (vigorous H$_2$ evolution). The resulting slurry was heated in an oil bath to 85° for 20 min (additional H$_2$ evolution). The slurry was cooled to rt, and a solution of ethyl bromoacetate (6.68 g, 40 mmol) in dry dimethylformamide (5 mL) was added dropwise from the addition funnel, during which time the precipitate cleared. The reaction was stirred 45 min, then was poured onto rapidly stirring water (320 mL). The resulting tan precipitate was isolated by filtration and washed with water. It was partitioned between water (50 mL) and dichloromethane (80 mL). The aqueous phase was extracted twice more with dichloromethane, and the combined extracts were washed with water then sat. NaCl, dried over Na$_2$SO$_4$, and filtered. The solvent was removed under reduced pressure, and the resulting solid was recrystallized from ethanol (50 mL), chilled, and filtered. The product was obtained as a white solid (5.3 g, 55%, mp 88.5°–89°). $^1$H NMR (CDCl$_3$) δ7.60 (4H, d, J=8.5), 6.75 (4H, d, J=8.5), 4.58 (4H, s), 4.25 (4H, q, J=7.1), 1.28 (6H, t, J=7.1). IR (KBr) 1765, 1720, 1580, 1480 cm$^{-1}$. FDMS (m/e) 488 (M$^+$, $^{130}$Te). Anal. calc'd for C$_{20}$H$_{22}$O$_6$Te: C, 49.43; H, 4.56. Found: C, 49.36; H, 4.55.

(e) Preparation of 4,4'-Di(carboxymethoxy)-1,1'-tellurobisbenzene, Disodium Salt (4)

Diester 4d (39.2 g, 81 mmol) was taken up in methanol (400 mL), and 10% aq NaOH (47 mL, 170 mmol) was added. A very thick slurry resulted. The reaction was heated to reflux for 1 h. The resulting slurry was cooled in an ice bath. The solid was isolated by filtration and washed with ethanol, air dried and ground with a mortar and pestle to give 4 as a pale cream solid (37.6 g, 98%). $^1$H NMR (DMSO-d$_6$, 5 drops D$_2$O) δ7.46 (4H, d, J=8.4), 6.66 (4H, d, J=8.5), 4.06 (4H, s). $^{13}$C NMR (D$_2$O) δ176.6, 158.0, 139.8, 115.9, 104.8, 66.5. IR (KBr) 3540 3430, 1595, 1490, 1415, 1230 cm$^{-1}$. Anal. calc'd for C$_{16}$H$_{12}$Na$_2$O$_6$Te.1.5 H$_2$O: C, 38.37; H, 3.02. Found: C, 38.33; H, 3.05.

Preparation 5. N,N,N',N'-Tetra(carboxymethyl)-4,4'-tellurobisbenzenamine, Tetrasodium Salt (5)

(a) Preparation of N-(2-Ethoxy-2-oxoethyl)-N-phenylglycine, Ethyl Ester (5a)

Aniline (9.3 g, 0.1 mol), ethyl bromoacetate (36.7 g, 0.22 mol), and 2,6-lutidine (23.5 g, 0.22 mol) in acetonitrile (200 mL) were refluxed 1 day in a flask equipped with a Newman tube. The reaction was complete by TLC (dichloromethane). It was cooled to rt and diluted with ether (200 mL). The precipitated lutidine hydrochloride was removed by filtration, and the filtrate was evaporated under reduced pressure. The residue was partitioned between ether and water, and the water layer was extracted twice more with ether. The combined extracts were washed with 1N HCL, water, sat. NaHCO$_3$, and sat. NaCl, dried over MgSO$_4$, and evaporated under reduced pressure to give crude 5a as a dark liquid. It was taken up in dichloromethane and filtered through silica gel to remove color, giving the product (23.2g, 88%) as a pale oil. $^1$H NMR (CDCl$_3$) δ7.21 (2H, t, J=7.9), 6.77 (1H, t, J=7.3), 6.61 (2H, δ, J=8.4), 4.20 (4H, q, J=7.2), 4.13 (4H, s), 1.26 (6H, t, J=7.1).

(b) Preparation of N,N,N',N'-Tetra(ethoxycarbonylmethyl)-4,4'-tellurobisbenzenamine (5b)

To a 500 mL 3-neck flask, oven-dried, equipped with an addition funnel and put under argon, was added tellurium (IV) chloride (11.9 g, 44 mmol). Dry ether (200 mL) was added by syringe, giving a thin yellow slurry, and the flask was placed in an ice bath. A solution of 5a (23.2 g, 89 mmol) in dry ether (50 mL) was prepared under argon, and the solution was transferred by cannula to the addition funnel. It was added dropwise to the reaction, with vigorous stirring. A thick sludge immediately formed and the stirring bar stopped. The remainder of the addition was performed while swirling and manually stirring the reaction. The reaction sat without stirring overnight, then was sonicated until all of the sludge was converted to a clumpy solid. The reaction was filtered, and the filter cake was washed with ether. The filter cake was taken up in dichloromethane (200 mL), and a solution of sodium metabisulfite (17.0 g, 89 mmol) in water (200 mL) was added with stirring. The resulting two-phase mixture was stirred 30 min. at rt. Solid NaHCO$_3$ was added to pH 7 and the reaction was filtered through Celite diatomaceous earth. The filtrate was transferred to a separatory funnel, the dichloromethane layer was split off, and the aqueous layer was extracted with additional dichloromethane. The combined extracts were washed with water and sat. NaCl, dried over $Na_2SO_4$, and filtered, and the solvent was removed under reduced pressure. The resulting red oil (17.9 g) was taken up in toluene (100 mL), and copper powder (9 g) was added. The reaction was heated to reflux with a Newman tube for 2 h. The resulting gray reaction was cooled to room temperature, filtered through Celite diatomaceous earth, and the solvent was removed under reduced pressure. The crude product (18 g amber oil) was flash chromatographed twice with dichloromethane then 98:2 dichloromethane:methanol to separate the product from recovered starting material, yielding pure 5b as a pale orange viscous oil (7.36 g, 50% of theory). $^1$H NMR ($CDCl_3$) δ7.52 (4H, d, J=8.6), 6.43 (4H, d, J=8.7), 4.19 (8H, q, J=7.1), 4.08 (8H, s), 1.25 (12H, t, J=7.1). $^{13}$C NMR ($CDCl_3$) δ170.7, 147.6, 139.5, 113.6, 101.3, 61.2, 53.3, 14.2. IR (salt plates) 1730, 1580, 1490, 1180 $cm^{-1}$. FDMS (m/e) 658 ($M^+$, $^{130}$Te).

(c) Preparation of N,N,N',N'-Tetra(carboxymethyl)-4,4'-tellurobisbenzenamine, Tetrasodium Salt (5)

Diester 5b (4.35 g, 6.63 mmol) was taken up in methanol (60 mL), and 10% aq NaOH (7.4 mL, 26.5 mmol) was added. The reaction was heated to reflux for 1 h. The resulting slurry was cooled in an ice bath, then filtered. The solid was washed with cold methanol and air dried, to give 5 as a pale cream solid (3.81 g, 91%). $^1$H NMR ($D_2O$) δ7.56 (4H, d, J=8.6), 6.38 (4H, d, J=8.6), 3.83 (8H, s). $^{13}$C NMR ($D_2O$) δ179.4, 148.7, 139.6, 113.0, 98.3, 55.5. IR (KBr) 3250 (br), 1575, 1405, 1210 $cm^{-1}$. Anal. calc'd for $C_{20}H_{16}Na_4N_2O_8Te \cdot 3H_2O$: C, 35.02; H, 3.23; N, 4.08. Found: C, 34.82; H, 3.03; N, 4.04.

The following examples illustrate the practice of this invention:

EXAMPLE 1

The coatings described were slit and mounted as slides. Cartridges containing the slides were prepared by placing the cartridges on the benchtop for 16–20 hours with the lights in the laboratory remaining on for this time period. On the day following the benchtop incubation, the slides were tested using a prototype automated thin-film immunoassay analyzer. Eleven uL of a human serum matrix solution containing 10,000 mIU/mL hCG was applied to each slide. Each slide was then incubated for 5 minutes at 37° C. after which 12 uL of a wash solution containing $Na_2HPO_4$ (10 mM, pH6.8), 4'-hydroxyacetanallide (5 mM), hexadecylpyridinium chloride (0.1%), $H_2O_2$ (8 mM), and diethylenetriamine-pentaacetic acid (DTPA) (10 µM) was applied to each slide. The wash fluid completes washing away unbound antibody-horseradish peroxidase label from the read area and serves to initiate the HRP-catalyzed dye formation reaction. Following addition of the wash solution each slide undergoes a second incubation at 37° C. during which time reflectance density readings are taken at intervals of 3 seconds at a wavelength of 670 nm. The rate of color formation for slides from each coating was calculated from the reflectance density readings.

Thin-film coatings for the assay of human chorionic gonadotropin (hCG) in serum samples of the following formulations were prepared on poly(ethylene terephthalate) support. (Terms used in all coating structures are described in Table 1)

Coating 1

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| Receptor Layer | TES Buffer, pH 7.0 | 0.10 |
| | TX-100 | 0.02 |
| | Polymer Binder | 0.80 |
| | Leuco Dye | 0.20 |
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Coating 2

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| | VO $SO_4$ | 0.04 |
| Receptor Layer | TES Buffer, pH 7.0 | 0.10 |
| | TX-100 | 0.02 |
| | Polymer Binder | 0.80 |
| | Leuco Dye | 0.20 |
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Coating 3

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| | DAT 1 | 0.04 |
| Receptor Layer | TES Buffer, pH 7.0 | 0.10 |
| | TX-100 | 0.02 |
| | Polymer Binder | 0.80 |
| | Leuco Dye | 0.20 |

-continued

| Layer | Material | Dry Coverage (g/m²) |
|---|---|---|
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Coating 4

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| | DAT 3 | 0.012 |
| Receptor Layer | TES Buffer, pH 7.0 | 0.10 |
| | TX-100 | 0.02 |
| | Polymer Binder | 0.80 |
| | Leuco Dye | 0.20 |
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Coating 5

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| | VO SO₄ | 0.04 |
| | DAT 1 | 0.04 |
| Receptor Layer | TES Buffer, pH 7.0 | 0.10 |
| | TX-100 | 0.02 |
| | Polymer Binder | 0.80 |
| | Leuco Dye | 0.20 |
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Coating 6

| Layer | Material | Dry Coverage (g/m²) |
|---|---|---|
| Bead Spread Layer | TES Buffer, pH 7.0 | 0.219 |
| | 3',5'-dichloro-4'-hydroxy-acetanilide | 0.22 |
| | Dimedone | 0.45 |
| | Adhesive Polymer | 2.58 |
| | Polymer Beads | 130.0 |
| | BSA | 1.0 |
| | Glycerol | 2.0 |
| | Mannitol | 1.0 |
| | Label | 34e-6 |
| | VO SO₄ | 0.04 |
| | DAT 3 | 0.012 |
| Receptor Layer | TES Buffer, pH 7.0 | 0.10 |
| | TX-100 | 0.02 |
| | Polymer Binder | 0.80 |
| | Leuco Dye | 0.20 |
| | Antibody Beads | 0.10 |
| | TETRONIC T908 | 0.02 |
| | OLIN 10G | 0.01 |
| Gel | Gelatin | 10.0 |
| | TES Buffer, pH 7.0 | 4.58 |
| | 3',5'-dichloro-4'-hydroxy-acetanilide | 0.44 |
| | TX-100 | 0.02 |
| | BVSME | 0.15 |

Cartridge Slide Comparison for Coatings 1–6

| Coating | Rate of Top Slides (n = 3) | Rate of Non-Top Slides (n = 15) | % Rate Loss of Top Slide |
|---|---|---|---|
| 1 | 0.186 Dt/Min | 0.231 Dt/Min | −19.48% |
| 2 | 0.316 Dt/Min | 0.317 Dt/Min | −0.32% |
| 3 | 0.305 Dt/Min | 0.318 Dt/Min | −4.09% |
| 4 | 0.202 Dt/Min | 0.211 Dt/Min | −4.27% |
| 5 | 0.292 Dt/Min | 0.295 Dt/Min | −1.02% |
| 6 | 0.211 Dt/Min | 0.212 Dt/Min | −0.47% |

The cartridge slide comparison clearly shows that a large percent rate loss occurs for the first slides in the cart when either VOSO$_4$ or the DAT compounds are not incorporated in the coating. This loss of rate of color formation in the first slide would result in an incorrect analyte concentration prediction for the sample being tested. The inclusion of VOSO$_4$ (coating 2), the DAT compounds (coatings 3 and 4) or the combination of VOSO$_4$ and the DAT compounds (coatings 5 and 6) results in marked improvement in the percent rate retained for the top slides.

EXAMPLE 2

In order to further differentiate the effects of the DAT compounds investigated, slides from each coating were placed face-up directly on the benchtop and exposed to the same conditions as the slides which remained in the cartridges (16–20 hour room temperature incubation with fluorescent lighting remaining on). Following the incubation period, the slides were tested on a prototype automated thin-film immunoassay analyzer using the same materials and protocol as described above. The expected result is a greater loss of rate of color formation due to the increased exposure of the slides to environmental factors (light, air, etc.). As a means of observing the effect of increased environmental exposure, the rate of color formation of the benchtop slides was compared to the rate of color formation of the cartridge slides for each condition (excluding the top slides). The results for the slides treated as described are as follows:

Cartridge Slide Comparison for Coatings 1–6

| Coating | Rate of Benchtop Slides (n = 10) | Rate of Cartridge Slides (n = 15) | % Rate Loss of Benchtop Slide |
| --- | --- | --- | --- |
| 1 | 0.161 Dt/Min | 0.231 Dt/Min | −30.3% |
| 2 | 0.288 Dt/Min | 0.317 Dt/Min | −9.15% |
| 3 | 0.293 Dt/Min | 0.318 Dt/Min | −7.86% |
| 4 | 0.179 Dt/Min | 0.211 Dt/Min | −15.17% |
| 5 | 0.291 Dt/Min | 0.295 Dt/Min | −1.36% |
| 6 | 0.198 Dt/Min | 0.212 Dt/Min | −6.6% |

The benchtop slide test shows again that inclusion of $VOSO_4$ (coating 2), the DAT compounds (coatings 3 and 4), or the combination of $VOSO_4$ and the DAT compounds (coatings 5 and 6) in the coating provides protection against rate loss due to environmental exposure. This test also shows that a cooperative function occurs when $VOSO_4$ and 1 are incorporated in the same coating (coating 5). This results in lower percent rate loss than when either compound is incorporated alone (coatings 2 and 3).

All DATs (1–5) were evaluated in a model system designed to accentuate the loss of HRP activity. In this system, DAT's 1, 4, and 5 protected HRP activity either alone or in cooperation with a vanadyl salt as shown in the next examples.

EXAMPLES 3–5

Analytical elements of the following formulation were prepared on a poly(ethylene terephthalate) support:

| Layer | Material | Dry Coverage (g/m$^2$) |
| --- | --- | --- |
| Bead Spread Layer | TES Buffer, pH 7.0 | 0.219 |
| | Adhesive Polymer | 2.58 |
| | Polymer Beads (20–40 µM) | 130.0 |
| Receptor Layer | Polymer Binder I | 0.60 |
| | TES Buffer, pH 7.0 | 0.10 |
| | TX-100 | 0.02 |
| Gel | Gelatin | 10.0 |
| | TES Buffer, pH 7.0 | 4.58 |
| | TX-100 | 0.020 |
| | BVSME | 0.150 |

This analytical element was used to measure HRP stability with the following protocol. Ten microliter samples of solutions of 10 mM sodium phosphate buffer, pH 7.0, containing about $3 \times 10^{-8}$ M HRP and varying amounts of one of the diaryl telluride compounds of the invention were spotted onto each of separate 1 cm$^2$ pieces of the above coated element (4 samples for each compound and at each concentration). These elements were dried and placed in a dark drawer. After 30 minutes and again after 24 hours, i.e., the next day, the elements were removed from the drawer and the HRP was extracted by immersing each element in 1 mL of a solution of 10 mM sodium phosphate buffer, 0.15M sodium chloride, 0.1% bovine serum albumin, pH 7.0, in a test tube to extract the HRP. After vortexing the test tube for 1 minute (which removed the analytical element components from the poly(ethylene terephthalate) support), the resulting suspension was centrifuged and the solution removed. The amount of active HRP in this solution was determined by adding a 100 µL aliquot to a spectrophotometer cuvette and a reagent solution to provide one mL of a final solution of 50 mM potassium phosphate buffer, pH 7.0, 5 mM 4'-hydroxyacetanilide, 0.625% Triton X-100 surfactant, 0.005% 4,5-bis(4-dimethylaminophenyl)-2-(4-hydroxy-3-methoxyphenyl)imidazole leuco dye, and 0.85 mM hydrogen peroxide. The assay temperature was 30° C. A blue color was formed whose rate was determined spectrophotometrically at 655 nm. The rate of color formation was directly proportional to the amount of active enzyme in the extract.

The data were expressed as activity ratios, calculated by dividing the activity extracted at 24 hours by the activity extracted at 30 minutes for each sample. A ratio of 1 indicated enzyme was fully protected by the additive over a 24 hour time period. Some run to run data variation was observed, which was probably caused by the day to day differences in environment humidity and temperature. This could affect how fast the HRP dried down on the coating and thus affect the enzyme's apparent stability. Therefore, data can be compared within the Examples 3–5, but not between any two of the examples.

EXAMPLE 3

Figure 1:
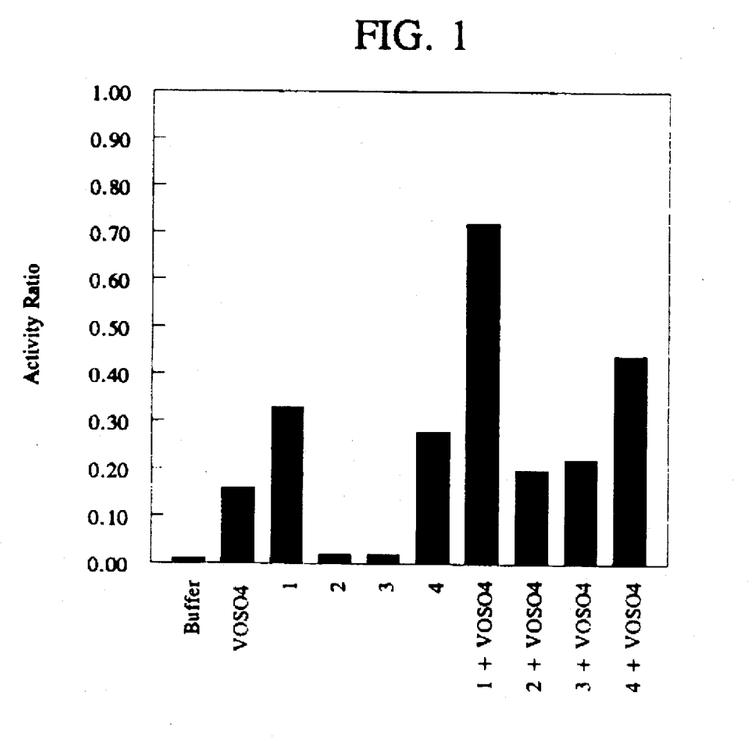
FIG. 1 is a bar-graph showing HRP stability in a model dry-down format when spotting solution variations included: buffer only, 1 mM VOSO4 and 1 mM each diaryl telluride alone or 1 mM of each with 1 mM VOSO4 as described in Example 3.

The effectiveness of compounds 1, 2, 3, and 4 at 1 mM is compared either alone or in the presence of 1 mM $VOSO_4$ (FIG. 1). Compounds 1 and 4 protected HRP activity in the model dry-down format relative to no additive. Compounds 2 and 3 were not effective stabilizers in this format. When both $VOSO_4$ and either 1 or 4 were included, more HRP activity was retained than in the presence of either one alone.

EXAMPLE 4

Figure 2:
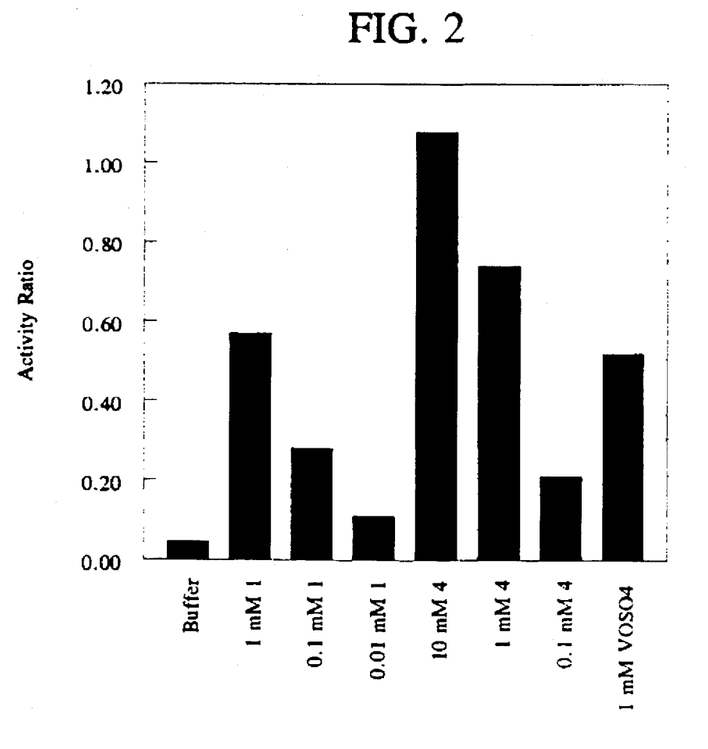
FIG. 2 is a bar-graph showing HRP stability over a 24 hour period in a model dry-down format with various concentrations of diaryl tellurides 1 and 4 as described in Example 4.

The effect of concentration on the ability of 1 and 4 to stabilize HRP is shown (FIG. 2). The following concentrations were used in the HRP solution: 1, 0.1 or 0.01 mM 1, and 10, 1, or 0.1 mM 4. In addition, HRP solutions containing buffer only, or 1 mM $VOSO_4$ were spotted. Activity loss was reagent concentration dependent for both 1 and 4. In the presence of 10 mM 4, HRP activity was fully protected after 24 hour incubation.

EXAMPLE 5

Figure 3:
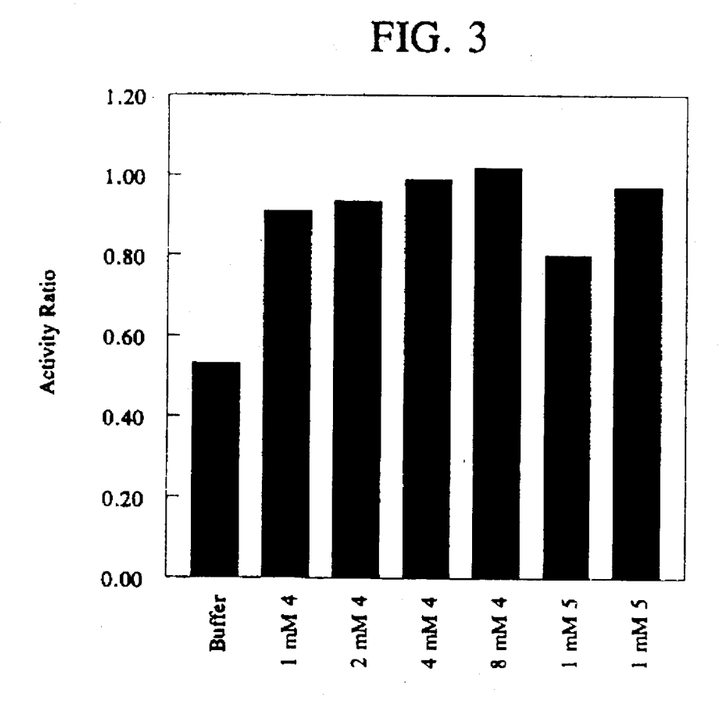
FIG. 3 is a bar-graph showing the stability of an anti-CRP-HRP conjugate in a model dry-down format with different concentrations of diaryl tellurides 4 and 5 incorporated in spotting solutions as described in Example 5.

This example shows the effect of 4 and 5 on the stability of anti-CRP-HRP enzyme conjugate ($2.85 \times 10^{-8}$ M). Also present in the spotting solution were buffer only; 1, 2, 4, or 8 mM 4; or 1 or 8 mM 5. Both 4 and 5 protected the activity of conjugated HRP, and the protection was concentration dependent (FIG. 3).

EXAMPLE 6

Coatings 7–10 were prepared as indicated in the following coating structures, 7–10, mounted as slides, conditioned at 70° F./33% RH for two days and frozen.

Coating 7

A thin-film coating for the assay of C-reactive protein (CRP) in serum samples of the following formulation was prepared on a poly(ethylene terephthalate) support.

| Layer | Material | Dry coverage (g/m$^2$) |
| --- | --- | --- |
| Bead Spread Layer | TES buffer | 0.219 |
| | Dimedone | 0.450 |
| | CaCl2 | 1.0 |
| | 3',5'-dicloro-4'-hydroxy-acetanilide | 0.22 |
| | glycerol | 2 |
| | bovine serum albumin | 0.5 |
| | magenta dye | 0.0538 |
| | adhesive polymer | 2.538 |
| | polymer beads | 130 |

| Layer | Material | Dry coverage (g/m²) |
|---|---|---|
| Receptor layer | TES buffer | 0.1 |
| | TX100 | 0.02 |
| | polymer binder | 0.8 |
| | leuco dye | 0.2 |
| | PC beads | 0.3 |
| | anti-CRP antibody | 0.05 |
| | anti-CRP antibody-HRP conjugate | 0.0005 |
| | TETRONIC T908 | 0.02 |
| | OLIN 10G | 0.01 |
| Gel | Gelatin | 10 |
| | TES buffer pH 7.0 | 4.580 |
| | 3'5'-dichloro-4'-hydroxy-acetanilide | 0.44 |
| | BSVME | 0.15 |

Coating 8

A thin-film coating for the assay of C-reactive protein (CRP) in serum samples of the following formulation was prepared on a poly(ethylene terephthalate) support.

| Layer | Material | Dry coverage (g/m²) |
|---|---|---|
| Bead Spread Layer | TES buffer | 0.219 |
| | Dimedone | 0.450 |
| | CaCl2 | 1.0 |
| | 3',5'-dicloro-4'-hydroxy-acetanilide | 0.22 |
| | glycerol | 2 |
| | bovine serum albumin | 0.5 |
| | magenta dye | 0.0538 |
| | adhesive polymer | 2.538 |
| | polymer beads | 130 |
| | DAT 1 | 0.08 |
| Receptor layer | TES buffer | 0.1 |
| | TX100 | 0.02 |
| | polymer binder | 0.8 |
| | leuco dye | 0.2 |
| | PC beads | 0.3 |
| | anti-CRP antibody | 0.05 |
| | anti-CRP antibody-HRP conjugate | 0.0005 |
| | TETRONIC T908 | 0.02 |
| | OLIN 10G | 0.01 |
| Gel | Gelatin | 10 |
| | TES buffer pH 7.0 | 4.580 |
| | 3'5'-dichloro-4'-hydroxy-acetanilide | 0.44 |
| | BSVME | 0.15 |

Coating 9

A thin-film coating for the assay of C-reactive protein (CRP) in serum samples of the following formulation was prepared on a poly(ethylene terephthalate) support.

| Layer | Material | Dry coverage (g/m²) |
|---|---|---|
| Bead Spread Layer | TES buffer | 0.219 |
| | Dimedone | 0.450 |
| | CaCl2 | 1.0 |
| | 3',5'-dicloro-4'-hydroxy-acetanilide | 0.22 |
| | gylcerol | 2 |
| | bovine serum albumin | 0.5 |
| | magenta dye | 0.0538 |
| | adhesive polymer | 2.538 |
| | polymer beads | 130 |
| | DAT 2 | 0.075 |
| Receptor layer | TES buffer | 0.1 |
| | TX100 | 0.02 |
| | polymer binder | 0.8 |
| | leuco dye | 0.2 |
| | PC beads | 0.3 |
| | anti-CRP antibody | 0.05 |
| | anti-CRP antibody-HRP conjugate | 0.0005 |
| | TETRONIC T908 | 0.02 |
| | OLIN 10G | 0.01 |
| Gel | Gelatin | 10 |
| | TES buffer pH 7.0 | 4.580 |
| | 3'5'-dichloro-4'-hydroxy-acetanilide | 0.44 |
| | BSVME | 0.15 |

Coating 10

A thin-film coating for the assay of C-reactive protein (CRP) in serum samples of the following formulation was prepared on a poly(ethylene terephthalate) support.

| Layer | Material | Dry coverage (g/m²) |
|---|---|---|
| Bead Spread Layer | TES buffer | 0.219 |
| | Dimedone | 0.450 |
| | CaCl2 | 1.0 |
| | 3',5'-dicloro-4'-hydroxy-acetanilide | 0.22 |
| | glycerol | 2 |
| | bovine serum albumine | 0.5 |
| | magenta dye | 0.0538 |
| | adhesive polymer | 2.538 |
| | polymer beads | 130 |
| | VOSO4 | 0.04 |
| Receptor layer | TES buffer | 0.1 |
| | TX100 | 0.02 |
| | polymer binder | 0.8 |
| | leuco dye | 0.2 |
| | PC beads | 0.3 |
| | anti-CRP antibody | 0.05 |
| | anti-CRP antibody-HRP conjugate | 0.0005 |
| | TETRONIC T908 | 0.02 |
| | OLIN 10G | 0.01 |
| Gel | Gelatin | 10 |
| | TES buffer pH 7.0 | 4.580 |
| | 3',5'-dichloro-4'-hydroxy-acetanilide | 0.44 |
| | BSVME | 0.15 |

Cartridges were thawed and loaded onto an E250 analyzer.

Eleven uL of a human serum sample containing about 20 mg/l CRP was applied to each slide. Each slide was then incubated for 5 minutes at 37° C. after which 12 uL of a wash solution containing Na2HPO4 (10 mM, pH 6.8), 4'-hydroxyacetanilide (5 mM), hexadecylpyddinium chloride (0.1%), H2O2 (8 mM), and DTPA (10 uM) was applied to each slide to wash the unbound antibody-HRP conjugate from the read area and initiate the HRP-catalyzed dye formation reaction. After 2.5 min. incubation at 37° C., the reflectance density at 670 nm is measured and converted to a concentration of CRP via a calibration curve.

The predicted concentration of the top slide was compared with the average predicted concentration of the next six slides. The results of several experiments of this type are shown below:

Bias=prediction top slide-prediction average of slides 2–7;

| Coating | Agent | Experiment 1 1 cart | Experiment 2; Average of 2 carts | Experiment 3 1 cart |
|---|---|---|---|---|
| 7 | none | −29.9 | −27.5 | −34.3 |
| 8 | 1 | −6.0 | −6.1 | −7.2 |
| 9 | 2 | −23.2 | −19.3 | −21.8 |
| 10 | VOSO$_4$ | −13.3 | −16.2 | −20.6 |

These results show that in the absence of any protective agent, the top slide has predicted value substantially less than the subsequent slides. Addition of either DTA 1 or 2 or VOSO$_4$ decreases the bias between the top slide and subsequent slides.

The greatest improvement is provided by 1.

EXAMPLE 7

Coatings 7–10 were slit, mounted as slides, conditioned at 70° F./33% RH for 2 days, and frozen.

Cartridges were thawed. The top slide of each cartridge was ejected and the cartridges were incubated at 70° F./33% RH for 3 days.

The slides were tested with human serum containing about 20 mg/l CRP as described in Example 6.

The prediction of the top slide receiving 3 days exposure at 70° F./33% RH was compared with the average prediction of slides 2–7 and the results are shown below:

Bias=prediction top slide-prediction average of slides 2–7;

| Coating | Agent | average of 2 carts |
|---|---|---|
| 7 | none | −26.4 |
| 8 | 1 | −4.5 |
| 9 | 2 | −8.2 |
| 10 | VOSO$_4$ | −5.6 |

These results show that a newly exposed top slide changes over a 3 day period resulting in a prediction that is substantially lower than subsequent slides in the absence of a protective agent. Diaryl tellurides 1 and 2 and VOSO$_4$ protect the slide and result in a smaller bias compared with subsequent slides in the cartridge, again 1 showing the greatest improvement.

EXAMPLE 8

Coatings 7–10 were slit, mounted as slides, conditioned at 70° F./33% RH for 2 days and frozen.

Cartridges were thawed and incubated at 70° F./33% RH for 7 days.

The incubated cartridges and freshly thawed cartridges were analyzed with 3 human serum samples containing CRP in the range of 10–30 mg/l as described in Example 6. The predictions of the incubated slides were compared with the predictions of the freshly thawed slides. The average bias of incubated vs freshly thawed slides for the 3 fluids was determined and is shown below.

| Coating | Agent | Average Bias |
|---|---|---|
| 7 | none | −7.8 |
| 8 | 1 | 0.8 |
| 9 | 2 | −2.62 |
| 10 | VOSO$_4$ | −0.26 |

These results show that, in the absence of a protective agent, slides exposed to 70° F./33% RH for 7 days develop a bias to freshly thawed slides. In the presence of either 1 or 2 or VOSO$_4$ the bias that results from this exposure is substantially reduced.

The invention results in improvement in HRP stability either alone or in conjunction with other stabilizers such as vanadyl compounds.

TABLE 1

| | |
|---|---|
| Adhesive Polymer | Poly(methyl acrylate-co-sodium 2-acrylamido-2-methylpropanesulfonate-co-2-acetoacetoxyethyl methacrylate). |
| Antibody Beads | Polymer particles of poly(styrene-co-3-(p-vinylbenzylthio)propionic acid having an antibody to human chorionic gonadotropin bound thereto. |
| PC Beads | Polymer particles of poly(styrene-co-3-(p-vinylbenzylthio)propionic acid having phosphoryl cholin bound thereto. |
| BSA | Bovine serum albumin. |
| BVSME | Bis(vinylsulfonylmethyl) ether. |
| DTPA | Diethylenetriaminepentaacetic acid. |
| Label | A conjugate of an anti-human chorionic gonadotropin antibody and thiolated horseradish peroxidase. |
| Leuco Dye | 4,5-Bis(4-dimethylaminophenyl)-2-(3,5-dimethoxy-4-hydroxyphenyl)imidazole. |
| Magenta Dye | 4,5-Dihydroxy-3-(6,8-disulfo-2-naphthylanzo)-2,7-naphthalenedisulfonic acid, sodium salt |
| MOPS | 3-(N-morpholino)propanesulfonic acid buffer. |
| OLIN 10G | An isononylphenoxypolyglycidol surfactant averaging about 10 glycidol units per molecule (sold by Olin Chemical Co). |
| Polymer Beads | Poly(vinyltoluene-co-methacrylic acid) particles having an average diameter of 20–40 μm. |
| Polymer Binder | Poly(N-isopropylacrylamide-co-2-acrylamido-2-methylpropane sulfonic acid sodium salt-co-N,N'-methylenebisacrylamide). |
| Polymer Binder I | Poly(N-isopropylacrylamide-co-2-hydroxyethyl methacrylate-co-N,N'-methylenebisacrylamide) |
| TES | N-[tris(hydroxymethyl)methyl]-2-aminoethanesulfonic acid buffer. |
| TX-100 | TRITON X-100 surfactant - an octylphenoxy polyethoxy ethanol surfactant (sold by Union Carbide). |
| TETRONIC T908 | A nonionic surfactant which is a block copolymer of ethylene oxide and propylene oxide (sold by BASF Corp). |

The invention has been described in detail with particular reference to preferred embodiments thereof, but it will be understood that variations and modifications can be effected within the spirit and scope of the invention.

We claim:

1. A dry immunoassay analytical element for assaying a ligand, comprising a support bearing:
   (a) a label zone comprising an enzyme labeled ligand or an enzyme labeled receptor;
   (b) a spreading zone comprising a diaryl telluride compound; and
   (c) a receptor zone comprising a fixed concentration of an immobilized receptor for the ligand and the labeled ligand when present, wherein the receptor is covalently bonded to polymeric beads having a diameter in the range of 0.1 to 5 μm; characterized in that the zones can be in the same or separate layers.

2. The element according to claim 1 wherein the diaryl telluride compound comprises a structure (I):

$Ar^1—Te—Ar^2$      (1)

wherein Ar¹ and Ar² represent the same or different aryl or heteroaryl groups, substituted or unsubstituted, having the following substituents:

wherein X is O, S, Se, or Te, and $R^{11}$, $R^{12}$, $R^{13}$, $R^{21}$, $R^{22}$, $R^{23}$, $R^{31}$, $R^{32}$, $R^{33}$, $R^{41}$, $R^{42}$ and $R^{43}$ are the same or different and each selected from the group consisting of hydrogen, alkyl having 1–5 carbon atoms, OH, $OR^1$, SH, $NH_2$, $NHR^1$, $NR^1{}_2$, $NR^1R^2$, $CO_2H$ or its salts, $CO_2R^1$, $SO_3H$ and its salts, $PO_3H_2$ and its salts, and $SR^1$ wherein $R^1$ and $R^2$ are different and each selected from the group consisting of alkyl having a carbon chain of 1 to 14 carbon atoms optionally carrying one or several hydrophilic groups, phenyl, and substituted phenyl.

$R^{14}$, $R^{15}$, $R^{24}$, and $R^{25}$ are the same or different and each selected from the group consisting of hydrogen, alkyl having 1–5 carbon atoms, alkoxy having 1–5 carbon atoms, $CO_2H$ or its salts, $CO_2R^1$, $SO_3H$ and its salts, $PO_3H_2$ and its salts.

3. The element according to claim 1 wherein horseradish peroxidase or a derivative of horseradish peroxidase is the label in the labeled ligand or labeled receptor.

4. A method for assaying an immunologically reactive ligand in an aqueous sample, comprising the steps of:

A. providing the dry immunoassay analytical element of claim 1;

B. contacting a finite area of the spreading zone of the element with the sample, thereby forming (i) an immobilized ligand-receptor complex, (ii) an immobilized enzyme labeled ligand-receptor complex, or (iii) a mixture of (i) and (ii), or an immobilized receptor-ligand-labeled receptor complex;

C. contacting the finite area with a substrate solution for the enzyme label thereby catalyzing the development of a color; and D. determining the concentration of the ligand colorimetrically.

5. A composition for use in an assay of an immunologically reactive ligand comprising (i) a diaryl telluride compound and (ii) horseradish peroxidase, a horseradish peroxidase labeled ligand, or a horseradish peroxidase labeled receptor.

6. The composition according to claim 5 wherein the compound is selected from the group consisting of:

and

7. The composition according to claim 6 wherein the compound is:

8. The composition according to claim 6 wherein the compound is:

9. The composition according to claim 6 wherein the compound is:

10. The composition according to claim 6 wherein the compound is:

11. The composition according to claim 6 wherein the compound is:

UNITED STATES PATENT AND TRADEMARK OFFICE
CERTIFICATE OF CORRECTION

PATENT NO. : 5,686,254
DATED : November 11, 1997
INVENTOR(S) : Margaret E. Logan et al.

It is certified that error appears in the above-indentified patent and that said Letters Patent is hereby corrected as shown below:

In column 27, line 31, kindly delete "." and insert --;--.

Signed and Sealed this

Tenth Day of March, 1998

Attest:

BRUCE LEHMAN

Attesting Officer

Commissioner of Patents and Trademarks